(12) United States Patent
Harman (10) Patent No.: US 11,826,026 B2
(45) Date of Patent: Nov. 28, 2023

(54) DENTAL ASPIRATION PREVENTION SYSTEMS AND METHODS

(71) Applicant: Bond Harman, Parker, CO (US)

(72) Inventor: Bond Harman, Parker, CO (US)

(*) Notice: Subject to any disclaimer, the term of this patent is extended or adjusted under 35 U.S.C. 154(b) by 0 days.

(21) Appl. No.: 17/721,159

(22) Filed: Apr. 14, 2022

(65) Prior Publication Data

US 2022/0330805 A1 Oct. 20, 2022

Related U.S. Application Data

(60) Provisional application No. 63/174,695, filed on Apr. 14, 2021.

(51) Int. Cl.
| | |
|---|---|
| *A61C 5/80* | (2017.01) |
| *A61C 17/10* | (2006.01) |
| *A61B 1/24* | (2006.01) |
| *A61C 5/88* | (2017.01) |
| *A61C 5/90* | (2017.01) |
| *A61C 5/82* | (2017.01) |
| *A61C 19/00* | (2006.01) |

(52) U.S. Cl.
CPC ............... *A61B 1/24* (2013.01); *A61C 5/82* (2017.02); *A61C 5/88* (2017.02); *A61C 5/90* (2017.02); *A61C 17/10* (2019.05); *A61C 19/001* (2013.01)

(58) Field of Classification Search
CPC ........... A61B 1/24; A61B 1/247; A61B 13/00; A61C 1/0061; A61C 17/02; A61C 17/06; A61C 17/08; A61C 17/092; A61C 17/10; A61C 19/001; A61C 5/80; A61C 5/82; A61C 5/88; A61C 5/90

USPC .................. 433/93, 138, 139, 140
See application file for complete search history.

(56) References Cited

U.S. PATENT DOCUMENTS

| | | | | | |
|---|---|---|---|---|---|
| 252,127 | A | * | 1/1882 | Morrill | A61B 13/00 600/240 |
| 465,716 | A | * | 12/1891 | Meister | A61C 5/82 433/139 |
| 647,574 | A | * | 4/1900 | Myers | A61C 5/82 433/137 |
| 730,038 | A | * | 6/1903 | Murlless | A61C 5/82 433/137 |

(Continued)

FOREIGN PATENT DOCUMENTS

CN 108524044 A 9/2018

OTHER PUBLICATIONS

International Search Report and Written Opinion dated Aug. 1, 2022 for corresponding PCT Application No. PCT/US2022/024887.

*Primary Examiner* — Cris L. Rodriguez
*Assistant Examiner* — Kylie M. Gaspar
(74) *Attorney, Agent, or Firm* — David Meibos; Maywood IP Law (57) ABSTRACT

In one embodiment, an aspiration prevention system is configured to keep items from moving from a mouth of a patient into a throat of the patient. The system includes a mouth prop, a frame, and an air-permeable barrier. The mouth prop has a top surface configured to abut top teeth of the mouth, a bottom surface configured to abut bottom teeth of the mouth, and a frame coupling feature. The frame has a barrier retention feature configured to retain an air-permeable barrier, and a prop coupling feature that is attachable to the frame coupling feature of the mouth prop in a position in which the frame at least partially covers the throat.

16 Claims, 9 Drawing Sheets

(56) References Cited

U.S. PATENT DOCUMENTS

| | | | | |
|---|---|---|---|---|
| 2,023,288 A * | 12/1935 | Pickett | A61C 5/90 | 600/238 |
| 2,563,361 A * | 8/1951 | Pohland | A61C 19/001 | D24/176 |
| 4,281,986 A * | 8/1981 | Erickson | A61C 17/08 | 433/136 |
| 4,544,357 A * | 10/1985 | Williams | A61C 19/00 | 433/136 |
| 4,820,155 A * | 4/1989 | Sauveur | A61B 46/00 | 433/136 |
| 4,889,491 A * | 12/1989 | Krygier | A61C 5/90 | 433/136 |
| 4,986,752 A * | 1/1991 | Graves | A61C 5/82 | 433/138 |
| 5,152,686 A | 10/1992 | Duggan et al. | | |
| 6,241,521 B1 * | 6/2001 | Garrison | A61B 1/24 | 433/140 |
| 6,267,591 B1 | 7/2001 | Barstow | | |
| 6,299,446 B1 * | 10/2001 | Ahlers | A61C 5/82 | 433/136 |
| 6,974,321 B2 * | 12/2005 | Hirsch | A61C 17/10 | 433/140 |
| 7,140,881 B1 * | 11/2006 | Gealon | A61C 5/90 | 433/136 |
| 7,963,286 B2 * | 6/2011 | Burdumy | A61B 13/00 | 433/140 |
| 8,292,620 B2 | 10/2012 | Black et al. | | |
| 8,303,305 B2 | 11/2012 | Sabbagh | | |
| 9,827,071 B2 * | 11/2017 | Braud | A61C 5/90 | |
| 10,925,590 B1 * | 2/2021 | Sumaily | A61B 1/07 | |
| 11,232,717 B2 * | 1/2022 | Wang | A61B 13/00 | |
| 2003/0031980 A1 * | 2/2003 | Owais | A61C 5/90 | 433/136 |
| 2004/0033468 A1 * | 2/2004 | Fischer | A61C 5/90 | 433/140 |
| 2009/0274991 A1 * | 11/2009 | Black | A61C 17/08 | 433/93 |
| 2014/0199655 A1 * | 7/2014 | Metzger | A61C 5/90 | 433/136 |
| 2015/0050616 A1 | 2/2015 | Hoye | | |
| 2016/0310234 A1 * | 10/2016 | Ritter | A61C 17/08 | |
| 2019/0060031 A1 * | 2/2019 | Mukherji | A61C 5/82 | |
| 2019/0142558 A1 * | 5/2019 | Walker | A61C 1/0007 | 433/92 |
| 2023/0031392 A1 * | 2/2023 | Lo Russo | A61B 1/247 | |

* cited by examiner

DENTAL ASPIRATION PREVENTION SYSTEMS AND METHODS

CROSS-REFERENCE TO RELATED APPLICATIONS

The present application claims the benefit of U.S. Provisional Application Ser. No. 63/174,695, entitled COMBINATION BITE-BLOCK/ASPIRATION PREVENTION TOOL, which was filed on Apr. 14, 2021. The foregoing is incorporated by reference as though set forth herein in its entirety.

TECHNICAL FIELD

The present disclosure relates to dental instruments and methods. More specifically, the present disclosure relates to systems and methods for preventing patient aspiration of dental implements during dental procedures.

BACKGROUND

Dentists often use isolation-related devices in order to help them access the oral environment while minimizing saliva contamination of the field and to prevent excess foreign material/liquid from entering the oral cavity. Current isolation techniques generally have several drawbacks. For example, they are commonly gag-inducing, uncomfortable, and/or suffocating to patients due to their limitation of airflow, and/or they take significant time to apply and remove from the patient. For this reason, dentists often omit these more cumbersome isolation techniques.

It is especially common to omit these tools for shorter appointments, appointments which require many breaks for intraoral radiography, or those procedures where water/aerosolized liquid is not used. These common procedures include crown/veneer cementation and try-in, implant impression and seating, calculus removal, and tooth extraction. Often, dentists will not use standard isolation techniques for these appointments because they are not using their water-producing hand piece or they do not need full saliva control. Failure to use isolation techniques often leads to aspiration of small items like veneers, crowns, bridges, implant abutments, screws, drivers, and exfoliated teeth.

To prevent this, the common protective technique taught in dental colleges and utilized for these procedures is to pack gauze between the posterior aspect of the dorsal tongue and the posterior soft palate. The gauze is bunched into a loose wad and simply rests in place. This technique comes with clear downsides. The patient may gag, swallow the gauze, push the gauze out of position with normal tongue movement, or worse, aspirate the gauze itself if the patient suddenly gasps or hiccups.

There is a clear need in the market for an easy-to-use device that reduces aspiration risk for the many procedures where traditional isolation techniques do not work, are too cumbersome to be utilized, or are unrealistic due to time requirements or patient acceptance. Dentists will inevitably turn to the quickest, easiest solutions like the aforementioned gauze packing. A better, faster, and more effective airway protection system that can be easily adopted and implemented by more providers would be utilized more, thus saving more patients from aspiration or ingestion of foreign bodies.

SUMMARY

The various systems and methods of the present disclosure have been developed in response to the present state of the art, and in particular, in response to the problems and needs in the art that have not yet been fully solved by currently available dental devices and methods. The systems and methods of the present disclosure may provide aspiration prevention for dental procedures, with enhanced comfort and convenience for the dentist and the patient.

To achieve the foregoing, and in accordance with the disclosure as embodied and broadly described herein, an aspiration prevention system may be configured to keep items from moving from a mouth of a patient into a throat of the patient. The system may include a mouth prop, a frame, and an air-permeable barrier. The mouth prop may have a top surface configured to abut top teeth of the mouth, a bottom surface configured to abut bottom teeth of the mouth, and a frame coupling feature. The frame may have a barrier retention feature configured to retain an air-permeable barrier, and a prop coupling feature that is attachable to the frame coupling feature of the mouth prop in a position in which the frame at least partially covers the throat.

The frame may have a first arm, a second arm, and a hinge configured to permit the second arm to pivot relative to the first arm such that the frame has an unfolded configuration in which the first arm is displaced from the second arm to permit insertion of the air-permeable barrier between the first arm and the second arm, and a folded configuration in which the first arm and the second arm extend adjacent to each other to capture the air-permeable barrier between the first arm and the second arm. The prop coupling feature may be attachable to the frame coupling feature in the folded configuration.

The frame coupling feature may be a slot. The prop coupling feature may include a first tab on the first arm, adjacent to the hinge, and a second tab of the second arm, adjacent to the hinge. The first tab, the second tab, and the hinge may be insertable into the slot in the folded configuration.

The barrier retention feature may have one or more holes that permit airflow between the throat and the mouth, through the one or more holes and through the air-permeable barrier.

The frame coupling feature may be a slot. The prop coupling feature may include a tab of the frame that is slidable into the slot.

The mouth prop may further have an airway aperture that permits airflow through the mouth prop with the frame coupling feature attached to the prop coupling feature.

The airway aperture may provide airflow into a cavity of the mouth prop from the throat. The frame coupling feature may be a slot anterior to the cavity. The prop coupling feature may include a tab of the frame that is slidable into the slot. The tab may have one or more holes that provide airflow between the cavity and the mouth.

The aspiration prevention system may further include the air-permeable barrier. The air-permeable barrier may be formed of a fabric material.

According to some embodiments, an aspiration prevention system may be configured to keep items from moving from a mouth of a patient into a throat of the patient. The aspiration prevention system may include a mouth prop, an air-permeable barrier, and a frame. The mouth prop may include a top surface configured to abut top teeth of the mouth, and a bottom surface configured to abut bottom teeth of the mouth. The frame may be configured to be attached to the mouth prop and configured to retain the air-permeable barrier, relative to the mouth prop, in a position in which the frame at least partially covers the throat.

The frame may include a first arm, a second arm, and a hinge configured to permit the second arm to pivot relative to the first arm such that the frame has an unfolded configuration in which the first arm is displaced from the second arm to permit insertion of the air-permeable barrier between the first arm and the second arm, and a folded configuration in which the first arm and the second arm extend adjacent to each other to capture the air-permeable barrier between the first arm and the second arm. The frame may be configured to be attached to the mouth prop in the folded configuration.

The mouth prop may be a slot. The frame may include a first tab on the first arm, adjacent to the hinge, and a second tab of the second arm, adjacent to the hinge. The first tab, the second tab, and the hinge may be insertable into the slot in the folded configuration.

The frame may have one or more holes that permit airflow between the throat and the mouth, through the one or more holes and through the air-permeable barrier.

The mouth prop may further have a cavity, a slot anterior to the cavity, and an airway aperture adjacent to the cavity. The airway aperture may provide airflow into the cavity from the throat. The frame may have a tab that is slidable into the slot. The tab may have one or more holes that provide airflow between the cavity and the mouth.

The air-permeable barrier may be formed of a fabric material.

According to some embodiments, an aspiration prevention system may be configured to keep items from moving from a mouth of a patient into a throat of the patient. The aspiration prevention system may include a mouth prop and a frame. The mouth prop may include a top surface configured to abut top teeth of the mouth, a bottom surface configured to abut bottom teeth of the mouth, and a frame coupling feature. The frame may have one or more holes that permit airflow through the frame, and a prop coupling feature that is attachable to the frame coupling feature of the mouth prop in a position in which the frame at least partially covers the throat.

The aspiration prevention system may further have an air-permeable barrier. The frame may be configured to retain the air-permeable barrier.

The frame may have a first arm, a second arm, and a hinge configured to permit the second arm to pivot relative to the first arm such that the frame has an unfolded configuration in which the first arm is displaced from the second arm to permit insertion of the air-permeable barrier between the first arm and the second arm, and a folded configuration in which the first arm and the second arm extend adjacent to each other to capture the air-permeable barrier between the first arm and the second arm. The prop coupling feature may be attachable to the frame coupling feature in the folded configuration.

The frame coupling feature may be a slot. The prop coupling feature may have a first tab on the first arm, adjacent to the hinge, and a second tab of the second arm, adjacent to the hinge. The first tab, the second tab, and the hinge may be insertable into the slot in the folded configuration.

The mouth prop may further have an airway aperture that permits airflow through the mouth prop with the frame coupling feature attached to the prop coupling feature.

The airway aperture may provide airflow into a cavity of the mouth prop from the throat. The frame coupling feature may be a slot anterior to the cavity. The prop coupling feature may include a tab of the frame that is slidable into the slot. The tab may have one or more holes that provide airflow between the cavity and the mouth.

These and other features and advantages of the present disclosure will become more fully apparent from the following description and appended claims, or may be learned by the practice of the disclosure as set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the claims set forth below, the exemplary embodiments of the disclosure will be described with additional specificity and detail through use of the accompanying drawings in which:

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1A through 9, is not intended to limit the scope of the disclosure, as claimed, but is merely representative exemplary of exemplary embodiments of the disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1:
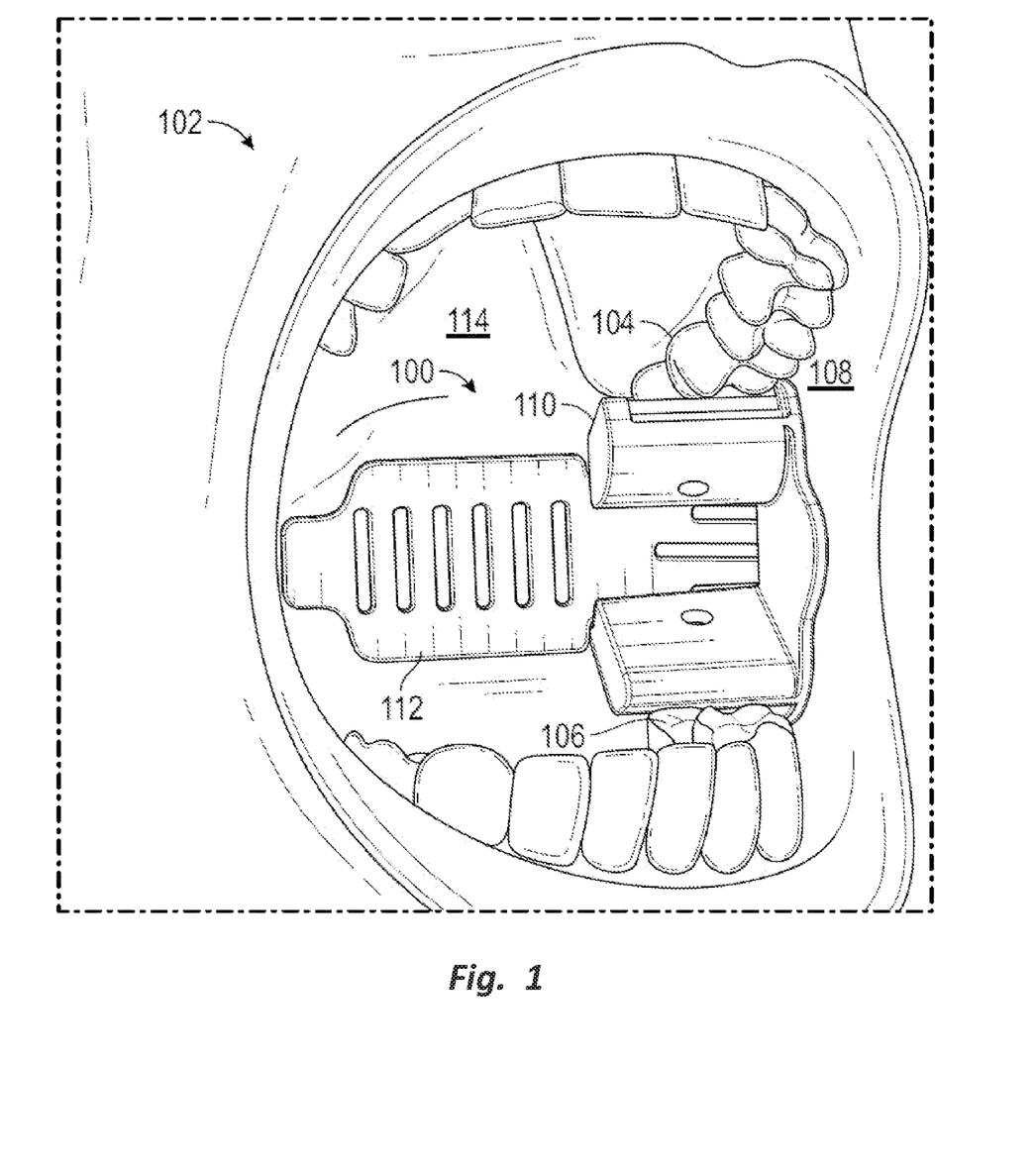
FIG. 1 is a perspective view of an aspiration prevention system according to one embodiment, in a mouth of a patient.
Figures 2A, 2B, 2C, 2D, 2E:
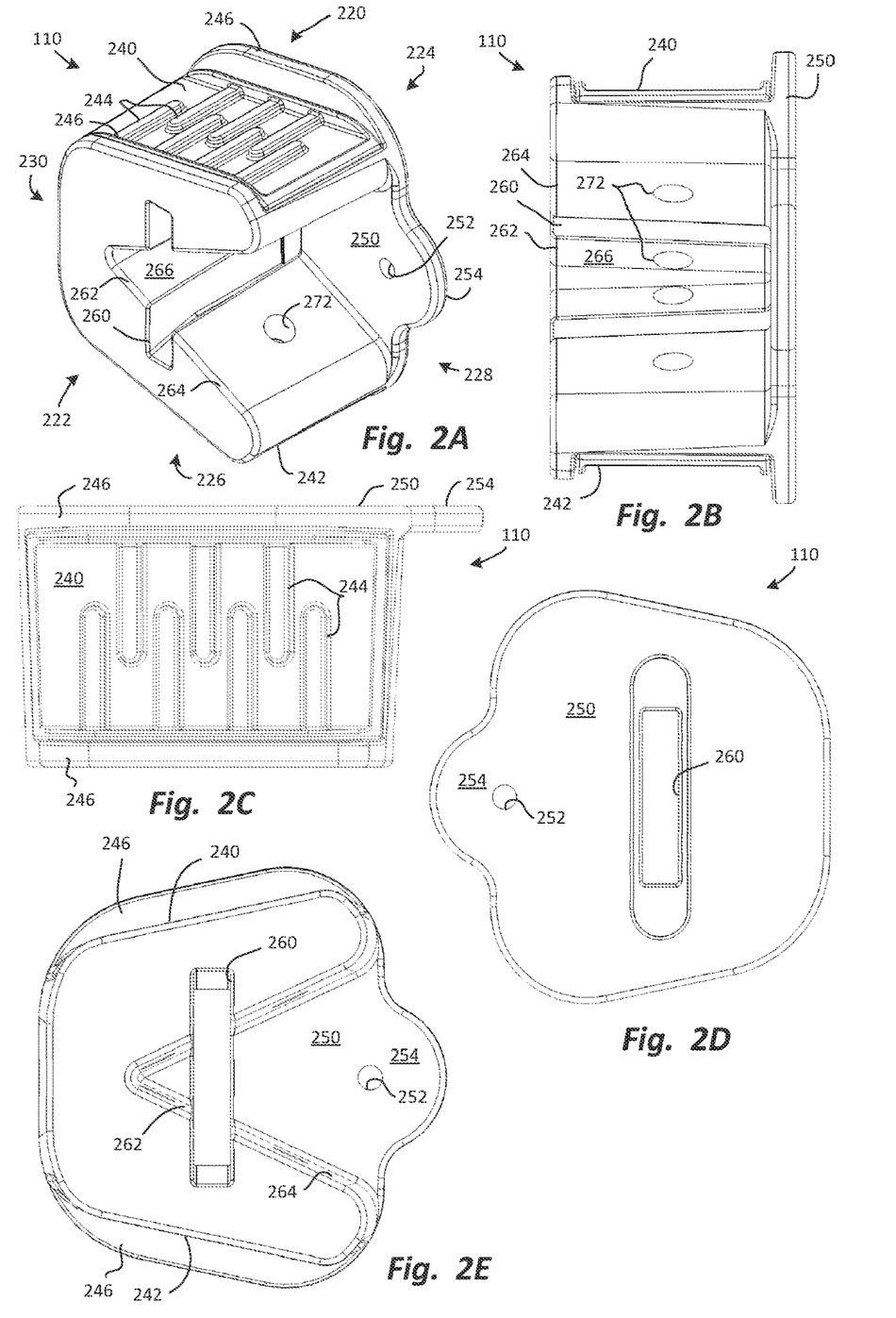
FIGS. 2A, 2B, 2C, 2D, and 2E are perspective, anterior, top, buccal, and lingual views, respectively, of the mouth prop of the aspiration prevention system of FIG. 1.

FIG. 1 is a perspective view of an aspiration prevention system 100 according to one embodiment, in a mouth 102 of a patient. As shown, the mouth 102 may have top teeth 104, bottom teeth 106, and a buccal mucosa 108 on the interior of the cheek. The patient may also have a throat, which is not visible in FIG. 1 as it is behind the aspiration prevention system 100. The aspiration prevention system 100 may be inserted into the mouth 102 to help prevent dental implements such as implants, fillings, small instruments, and the like, from being aspirated, i.e., dropped from the mouth 102 into the throat, of the patient.

In addition to aspiration prevention, the aspiration prevention system 100 may help hold the mouth 102 open to facilitate performance of one or more dental procedures in the mouth 102. Thus, the aspiration prevention system 100 may have a mouth prop 110 that helps hold the mouth 102 open in addition to providing an anchor for other components of the aspiration prevention system 100. Further, the aspiration prevention system 100 may have a frame 112 attached to the mouth prop 110, and a barrier 114 attached to the frame 112.

The barrier 114 may be arranged between the mouth 102 and the patient's throat to catch any items inadvertently dropped within the mouth 102. The barrier 114 may advantageously be flexible to enhance the patient's comfort and facilitate use of the aspiration prevention system 100 with different patients and procedures. Further, the barrier 114 may be air-permeable so that the patient can breathe through the barrier 114. The barrier 114 may further be disposable if desired. In some embodiments, the barrier 114 may be a fabric. For example, the barrier 114 may be a piece of gauze, such as a two-inch square or three-inch square piece. In alternative embodiments, the barrier 114 may have a shape that is more closely matched to the shape of the mouth 102. For example, the barrier 114 may be circular, oval, or otherwise shaped to fit the space between the mouth 102 and the throat. In yet other alternative embodiments, the barrier 114 may be contoured to match the shape of the frame 112.

The frame 112 may be secured to the barrier 114 to hold the barrier 114 in position. The frame 112 may also advantageously be air-permeable. Further, the frame 112 may be anchored to the mouth prop 110, which may also be air-permeable. The mouth prop 110 and/or the frame 112 may be formed of lightweight materials that can safely reside in the mouth 102 for the duration of a dental procedure. For example, various plastic materials may be used, including but not limited to Polyethylene, Polypropylene, ABS, Polycarbonate, PEEK, and/or the like. The mouth prop 110 and the frame 112 may be formed of the same or different materials.

FIGS. 2A, 2B, 2C, 2D, and 2E are perspective, anterior, top, buccal, and lingual views, respectively, of the mouth prop 110 of the aspiration prevention system 100 of FIG. 1. As shown, the mouth prop 110 may have a top 220, a bottom 222, a buccal side 224, a lingual side 226, an anterior end 228, and a posterior end 230.

The mouth prop 110 may further have a top surface 240 shaped to rest against and support the top teeth 104, and a bottom surface 242 shaped to rest against and support the bottom teeth 106. The mouth prop 110 may be shaped to keep the top surface 240 and the bottom surface 242 in place on the top teeth 104 and the bottom teeth 106. For example, the mouth prop 110 may have ridges 244 and/or other frictional engagement features, such as bumps, grid patterns, or the like, to keep the top surface 240 and the bottom surface 242 from slipping off of the top teeth 104 and the bottom teeth 106. Further, the mouth prop 110 may have side walls 246 adjacent to the top surface 240 and the bottom surface 242, on the buccal side 224 and the lingual side 226, to keep the mouth prop 110 from slipping medially or laterally off of the top teeth 104 and the bottom teeth 106.

The mouth prop 110 may further have a buccal wall 250 that provides a flat, non-abrasive surface to be positioned adjacent to the buccal mucosa 108 of the patient. The buccal wall 250 may have a hole 252 adjacent to a flange 254 extending anteriorly from the remainder of the buccal wall 250.

The mouth prop 110 may have a slot 260 that extends laterally from the lingual side 226. The slot 260 may optionally extend through the entire width of the mouth prop 110, to the buccal side 224. The slot 260 may have a generally rectangular cross-sectional shape. The lingual side 226 may further have a posterior aperture 262 and an anterior aperture 264. The posterior aperture 262 and the anterior aperture 264 may be separated from each other by the slot 260, and may cooperate to define a generally triangular shape that grows wider toward the anterior end 228 of the mouth prop 110. A cavity 266, posterior to the slot 260, may be accessible through the posterior aperture 262. The mouth prop 110 may optionally have holes 272 in the interior surfaces adjacent to the cavity 266 and the space anterior to the cavity 266.

Figure 3A:
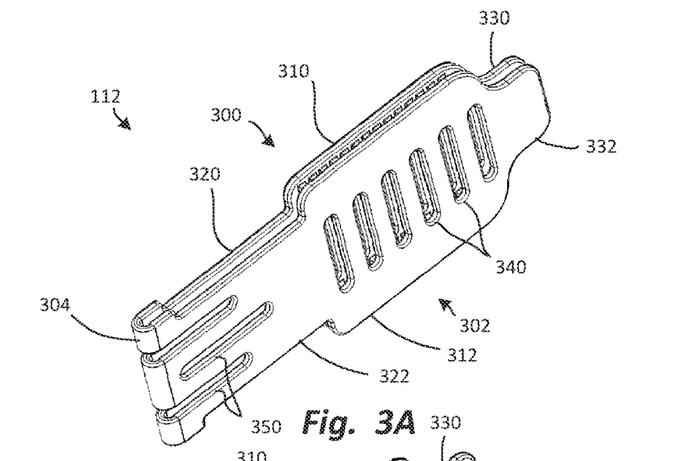
FIGS. 3A, 3B, and 3C are perspective views of the frame of the aspiration prevention system of FIG. 1, in a folded position, a partially folded position, and an open position, respectively.
Figure 3B:
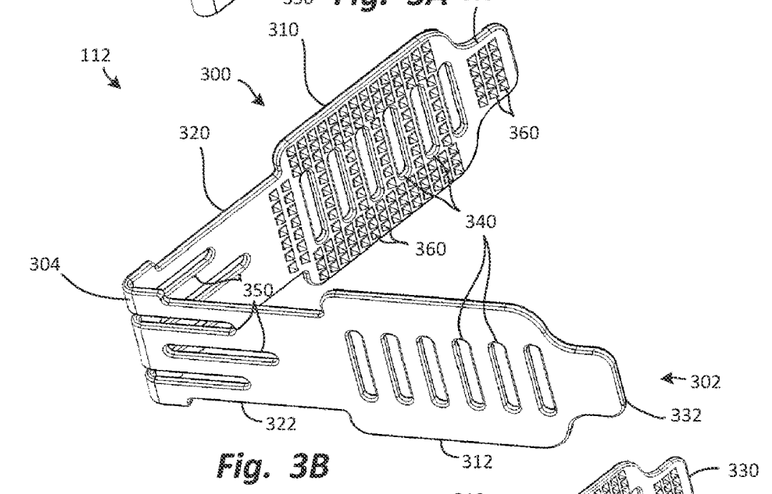
Figure 3C:
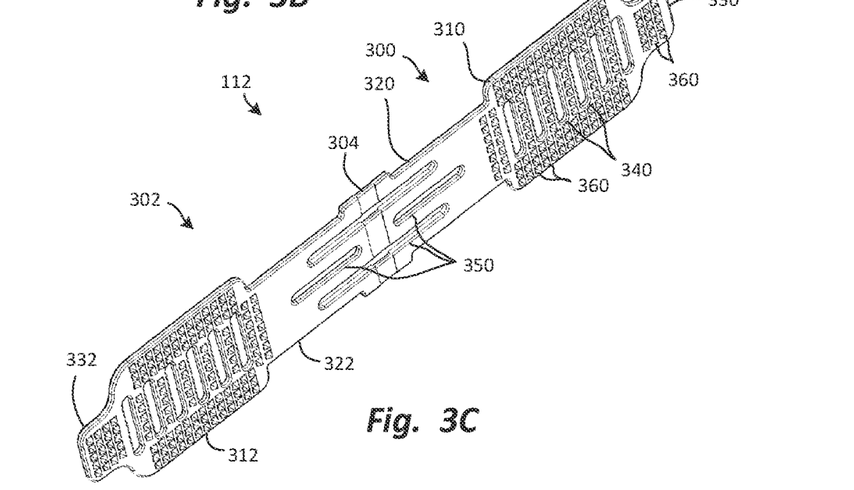

FIGS. 3A, 3B, and 3C are perspective views of the frame 112 of the aspiration prevention system 100 of FIG. 1, in a folded position, a partially folded position, and an open position, respectively. As shown, the frame 112 may have a first arm 300 and a second arm 302, which may be pivotably coupled to each other such that the frame 112 can be moved between the folded position of FIG. 3A to the open position of FIG. 3C, via the partially folded position of FIG. 3B. Specifically, the first arm 300 and the second arm 302 may be connected together via a hinge 304. The hinge 304 may be, for example, a living hinge. In alternative embodiments, a hinge may be defined by a pin joint or other mechanical construct.

The first arm 300 may have a first grip portion 310, and the second arm 302 may have a second grip portion 312. The first grip portion 310 and the second grip portion 312 may cooperate to grip the barrier 114 in the folded position. For example, at least a portion of the barrier 114 may be inserted between the first grip portion 310 and the second grip portion 312 in the partially folded position, and then the frame 112 may be moved to the folded position to capture the portion of the barrier 114 between the first grip portion 310 and the second grip portion 312.

The first arm 300 and the second arm 302 may further have a first tab 320 and a second tab 322, respectively. The first tab 320 and the second tab 322 may be positioned adjacent to and on either side of the hinge 304. The first tab 320 may be between the hinge 304 and the first grip portion 310, and the second tab 322 may be between the hinge 304 and the second grip portion 312. The first tab 320 and the second tab 322 may be sized to be insertable, together (i.e., in the folded position) into the slot 260 of the mouth prop 110, as will be shown in FIG. 4.

The first arm 300 and the second arm 302 may further have a first flange 330 and a second flange 332. The first flange 330 and the second flange 332 may be positioned at the outer ends of the first arm 300 and the second arm 302, and may extend from the first grip portion 310 and the second grip portion 312, respectively. The first flange 330 and the second flange 332 may be sized to be easily gripped (for example, between a finger and thumb) to facilitate moving the frame 112 between the folded and unfolded positions. For example, the practitioner may easily insert fingernails or thumbnails between the first flange 330 and the second flange 332 in order to pry them apart to withdraw the barrier 114. In some embodiments, the frame 112 may be made to snap into the folded configuration (for example, via integrated snaps or other fasteners—not shown) so that it may be beneficial for the user to apply some leverage on the first flange 330 and the second flange 332 to pull the first grip portion 310 and the second grip portion 312 apart.

The frame 112 may be made to facilitate airflow through the aspiration prevention system 100. For example, the first grip portion 310 and the second grip portion 312 may both be air-permeable so that air passing through the barrier 114, gripped between the first grip portion 310 and the second grip portion 312, is also able to pass through the first grip portion 310 and the second grip portion 312. Thus, the first grip portion 310 may have holes 340 and the second grip portion 312 may also have holes 340 that are aligned with the holes 340 of the first grip portion 310 when the frame 112 is in the folded position so that air can flow through the first grip portion 310, the barrier 114, and the second grip portion 312. The holes 340 may have any desired shape, including the oblong slots illustrated in FIGS. 3A, 3B, and 3C.

In alternative embodiments, more or fewer holes 340 may be present in the first grip portion 310 and/or the second grip portion 312. In some embodiments, the first grip portion 310 and the second grip portion 312 may have a mesh shape with a pattern of interstitial holes. In some alternative embodiments, the first grip portion 310 and the second grip portion 312 may have only a single hole. For example, the first grip portion 310 and/or the second grip portion 312 may each have the shape of a box, ring, or other shape defining a single central opening. In still other embodiments, the first grip portion 310 and/or the second grip portion 312 may have holes that are not fully bounded (i.e., not fully surrounded by material). For example, the first grip portion 310 and/or the second grip portion 312 may have slots that extend from the perimeter of the first grip portion 310 and/or the second grip portion 312, into the interior thereof. In this application, the word "hole" includes such openings that are not fully bounded.

The first tab 320 and/or the second tab 322 may also be designed to permit airflow therethrough in order to facilitate airflow through the mouth prop 110. For example, the first tab 320 may have holes 350, and the second tab 322 may also have holes 350 that are aligned with the holes 350 of the first tab 320 when the frame 112 is in the folded position. So that air can flow through the mouth prop 110, the first tab 320, and the second tab 322, as will be further described in connection with FIG. 4. Any of the variations set forth above for the holes 340 may also be used for the holes 350 in the first tab 320 and/or the second tab 322.

The interior-facing surfaces of the first arm 300 and the second arm 302 may have features that help retain the barrier 114 between the first grip portion 310 and the second grip portion 312. For example, teeth 360 may be distributed along the interior surfaces of the first grip portion 310 and the second grip portion 312. Additionally or alternatively, the teeth 360 may be present on the interior surfaces of the first tab 320 and the second tab 322, and/or the first flange 330 and the second flange 332. The teeth 360 may be generally pyramidal in shape, with points on the first arm 300 that fold against corresponding points on the second arm 302 to securely retain the barrier 114 between the first grip portion 310 and the second grip portion 312.

In alternative embodiments, the teeth 360 may be arranged in different patterns. For example, the teeth 360 of the first arm 300 may align with the spaces between the teeth 360 of the second arm 302 to crinkle the barrier 114 between the first grip portion 310 and the second grip portion 312, providing for more secure retention. Additionally or alternatively, various other retention structures, such as ridges, snaps, clasps, grooves, and/or the like may be used. In yet other alternative embodiments, the interior-facing surfaces of the first arm 300 and the second arm 302 may be smooth, and the first arm 300 and the second arm 302 may simply come together tightly enough to retain the barrier 114 without surface features. In yet other embodiments, additional fastening devices such as various clips, clamps, and/or the like may be used to hold the barrier 114 in place relative to the frame 112.

Figure 4:
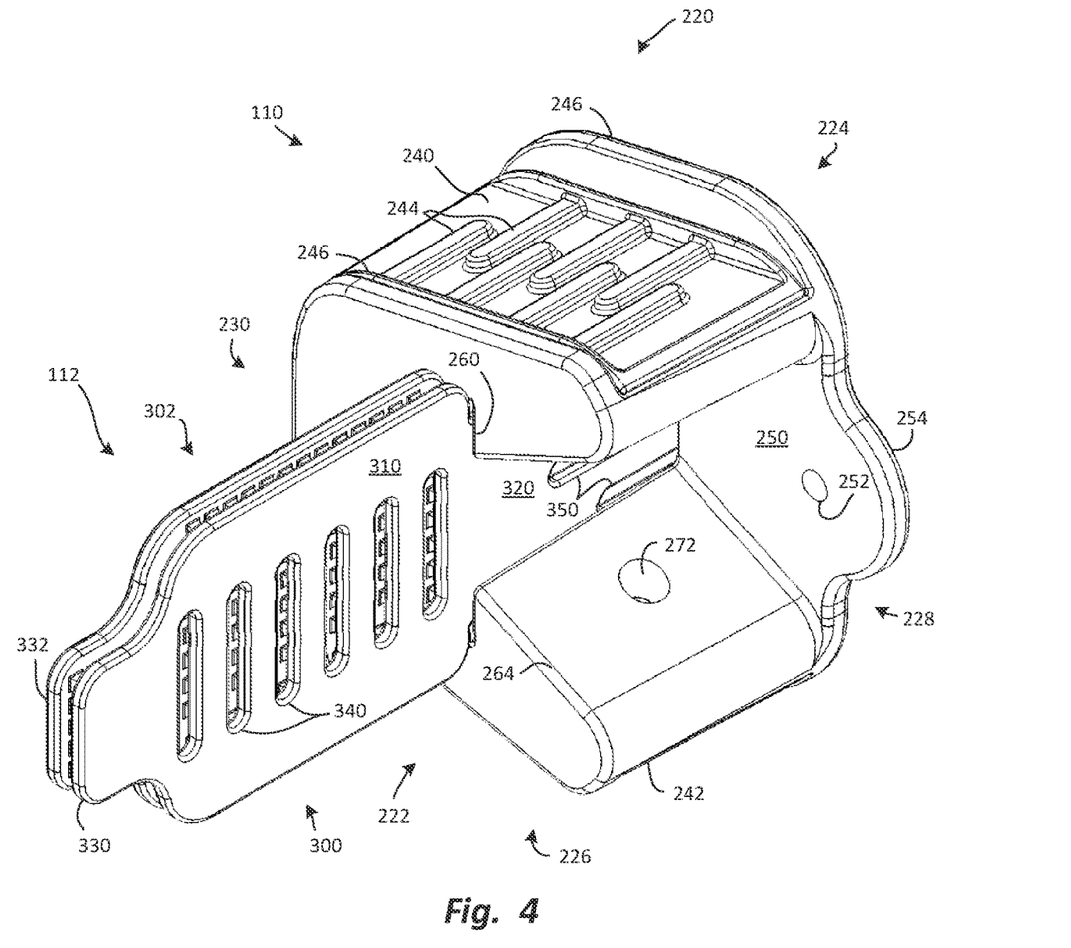
FIG. 4 is a perspective view of the mouth prop and frame of the aspiration prevention system of FIG. 1.

FIG. 4 is a perspective view of the mouth prop 110 and frame 112 of the aspiration prevention system 100 of FIG. 1. The frame 112 is in the folded position, and is attached to the mouth prop 110. The barrier 114 may be captured between the first grip portion 310 and the second grip portion 312 as described above, but is not shown in FIG. 4.

More precisely, the frame 112 has been moved to the closed position and the inboard ends of the first arm 300 and the second arm 302 have been inserted into the slot 260 of the mouth prop 110. Yet more precisely, the hinge 304 has been inserted into the slot 260 first, from the lingual side 226, followed by the first tab 320 and the second tab 322 of the first arm 300 and the second arm 302, respectively. The first grip portion 310 and the second grip portion 312, along with the barrier 114, may remain outside of the mouth prop 110. The hinge 304 may not move far enough through the slot 260 to protrude from the buccal side 224.

According to one method of use, the aspiration prevention system 100 may be operated as follows. With the mouth prop 110, the frame 112, and the barrier 114 disassembled, the frame 112 may be moved to the unfolded position or the partially folded position. The barrier 114 may be positioned adjacent to the first grip portion 310 and/or the second grip portion 312 or between the first grip portion 310 and the second grip portion 312. The frame 112 may be moved to the closed position to capture the barrier 114 between the first grip portion 310 and the second grip portion 312. The frame 112 may be attached to the mouth prop 110, for example, by inserting the hinge 304, and then the first tab 320 and the second tab 322, into the slot 260. Then, the mouth prop 110 may be inserted into the mouth 102 and placed such that the top surface 240 abuts the top teeth 104 and the bottom surface 242 abuts the bottom teeth 106, and the frame 112 and the barrier 114 separate the throat from the mouth 102 as shown in FIG. 1.

In alternative embodiments, the aspiration prevention system 100 may be assembled in-situ. For example, the mouth prop 110 may be inserted into the mouth 102 without the frame 112 and the barrier 114 attached thereto. The mouth prop 110 may optionally be used to facilitate dental procedures for which aspiration protection is not needed. Then, the frame 112 and the barrier 114 may be assembled either inside or outside the mouth, and then attached to the mouth prop 110 with the mouth prop 110 already in place within the mouth 102.

Once the aspiration prevention system 100 has been assembled, the first grip portion 310, the second grip portion 312, and the barrier 114 may generally be positioned in the patient's airway, between the mouth 102 and the throat. Thus, the first grip portion 310, the second grip portion 312, and/or the barrier 114 may catch items dropped in the mouth 102 that could otherwise enter the throat.

The holes 350 of the first tab 320 and the second tab 322 may facilitate airflow through the mouth prop 110. Specifically, air may flow between the patient's throat and the cavity 266 through the posterior aperture 262. Air may also flow between the cavity 266 and the mouth 102 through the holes 350 of the first tab 320 and the second tab 322. Thus, the holes 350, the cavity 266, and the posterior aperture 262 may cooperate to provide supplemental airflow, in addition to that provided by the holes 340 and the air permeability of the barrier 114. Such additional airflow may help the patient feel more at ease during the dental procedure, avoiding the reflex that can occur when there is a perception of inadequate airflow.

The slot 260 may act as a frame coupling feature by facilitating coupling of the frame 112 to the mouth prop 110. Similarly, the first tab 320 and the second tab 322 may act as prop coupling features by facilitating coupling of the mouth prop 110 to the frame 112. In alternative embodiments, a wide variety of frame coupling features and prop coupling features may be used. These features may include any fastening devices known in the art, including but not limited to clips, clamps, screws, nuts, bolts, snap fasteners, and/or the like. In other alternative embodiments, the frame 112 may be combined with the mouth prop 110. The mouth prop 110 and the frame 112 may then be formed as a single piece.

In some embodiments, the first grip portion 310 and the second grip portion 312 may be sufficiently large, and the holes 340 may be sufficiently narrow, to permit the mouth prop 110 and the frame 112 to provide adequate protection against aspiration without the barrier 114. Thus, the barrier 114 may be omitted in some embodiments. Similarly, in alternative embodiments, the barrier 114 may be secured to the mouth prop 110 without the frame 112, or may be secured to other implements, so that the frame 112 can be omitted. In yet other alternative embodiments, the mouth prop 110 may be omitted in favor of attachment of the frame 112 to one or more other structures, or attachment of the frame 112 directly to the mouth 102. One embodiment of a frame with enlarged grip portions will be shown and described on connection with FIGS. 5 through 7.

Figure 5:
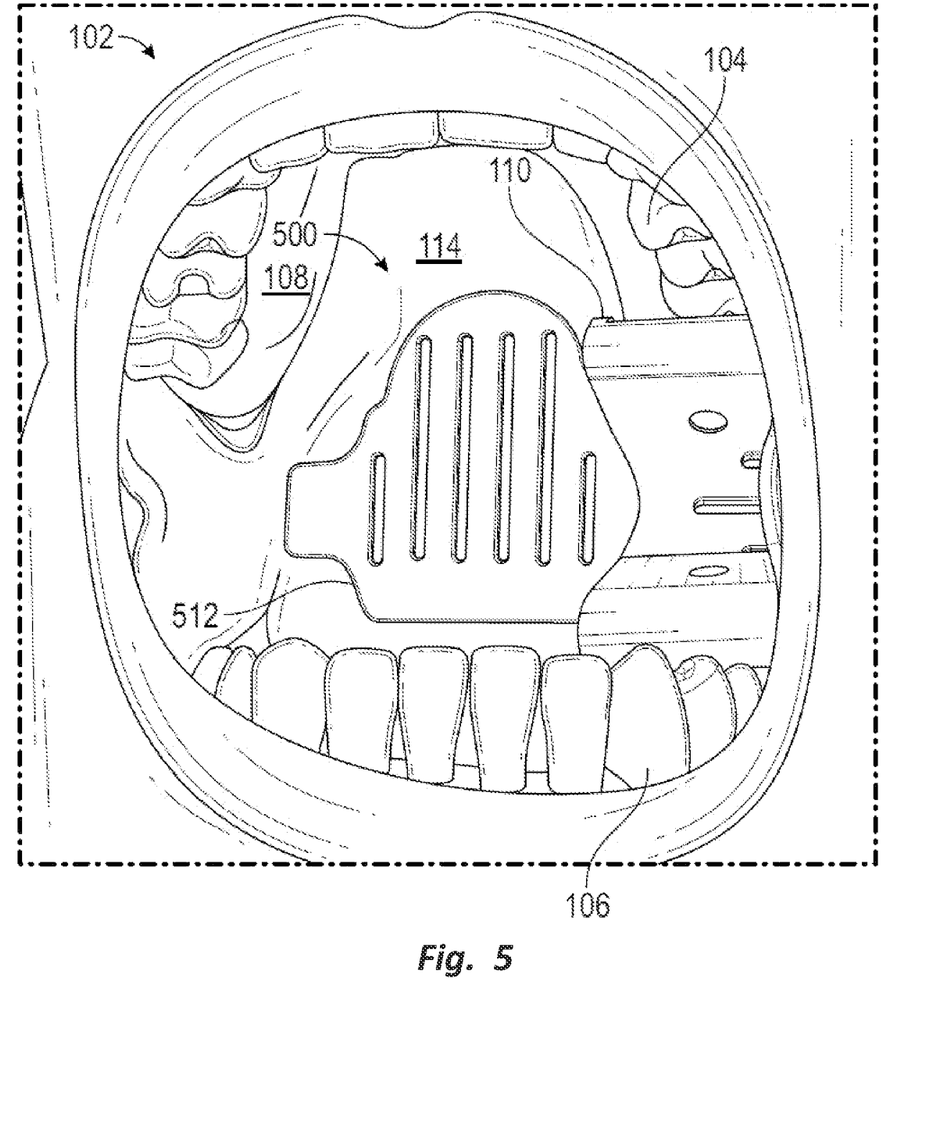
FIG. 5 is a perspective view of an aspiration prevention system according to another embodiment, in a mouth of a patient.

FIG. 5 is a perspective view of an aspiration prevention system 500 according to another embodiment, in a mouth 102 of a patient. Like the aspiration prevention system 100 of FIGS. 1 through 4, the aspiration prevention system 500 may include a mouth prop 110, a frame 512, and a barrier 114. The mouth prop 110 and the barrier 114 may be the same as in the aspiration prevention system 100, although the barrier 114 may optionally be omitted. The frame 512 may be shaped differently from the frame 112, as will be shown in greater detail in FIGS. 6A, 6B, and 6C.

Figure 6A:
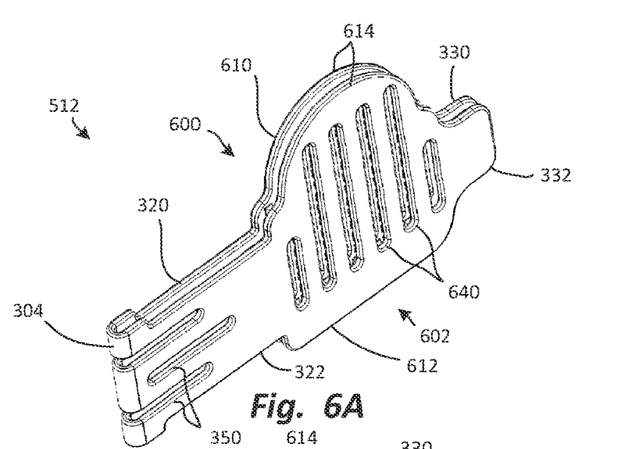
FIGS. 6A, 6B, and 6C are perspective views of the frame of the aspiration prevention system of FIG. 5, in a folded position, a partially folded position, and an open position, respectively.
Figure 6B:
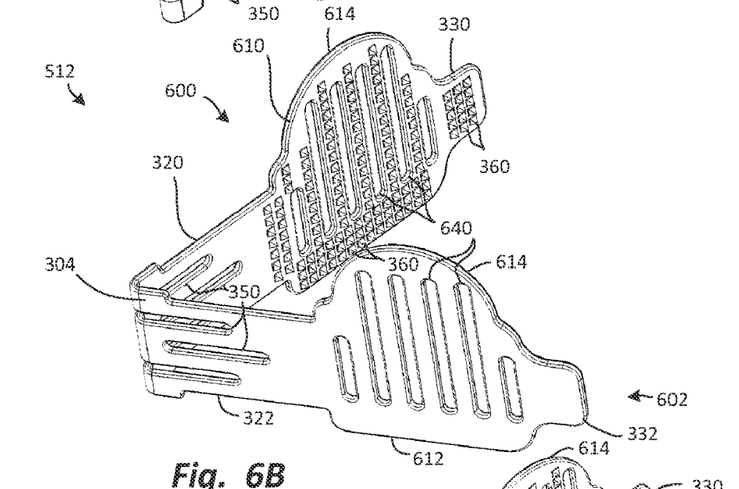
Figure 6C:
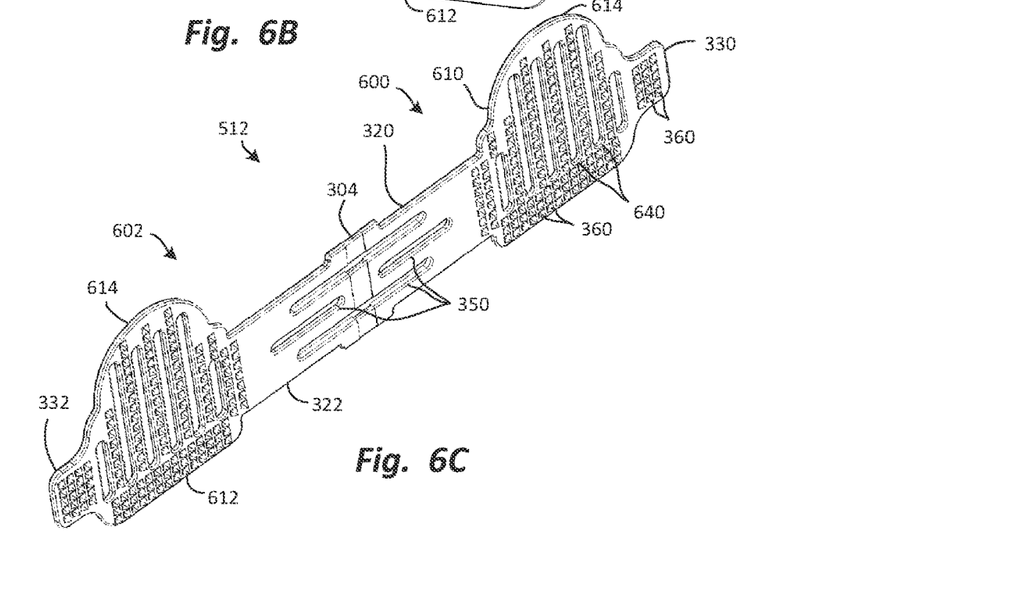

FIGS. 6A, 6B, and 6C are perspective views of the frame 512 of the aspiration prevention system 500 of FIG. 5, in a folded position, a partially folded position, and an open position, respectively. As shown, the frame 512 may have a first arm 600 and a second arm 602. The first arm 600 and the second arm 602 may be connected together via a hinge 304, like the first arm 300 and the second arm 302 of the frame 112. However, the first arm 600 and the second arm 602 may have a first grip portion 610 and a second grip portion 612 that each include an enlarged extension 614, making them extend further toward the roof of the mouth 102 than their counterparts of the frame 112. The rounded shape of the extensions 614 may generally conform to the shape of the roof of the mouth 102, helping the first grip portion 610 and the second grip portion 612 more completely block the patient's airway.

Thus, the frame 512 may provide enhanced aspiration protection relative to the frame 112. As mentioned previously, this protection may allow the frame 512 to be used without the barrier 114. However, the barrier 114 may also be used in combination with the frame 512, as shown in FIG. 5.

The remaining features of the aspiration prevention system 500 may be substantially the same as described above in connection with the aspiration prevention system 100. The aspiration prevention system 500 may be used in substantially the same manner.

Figure 7:
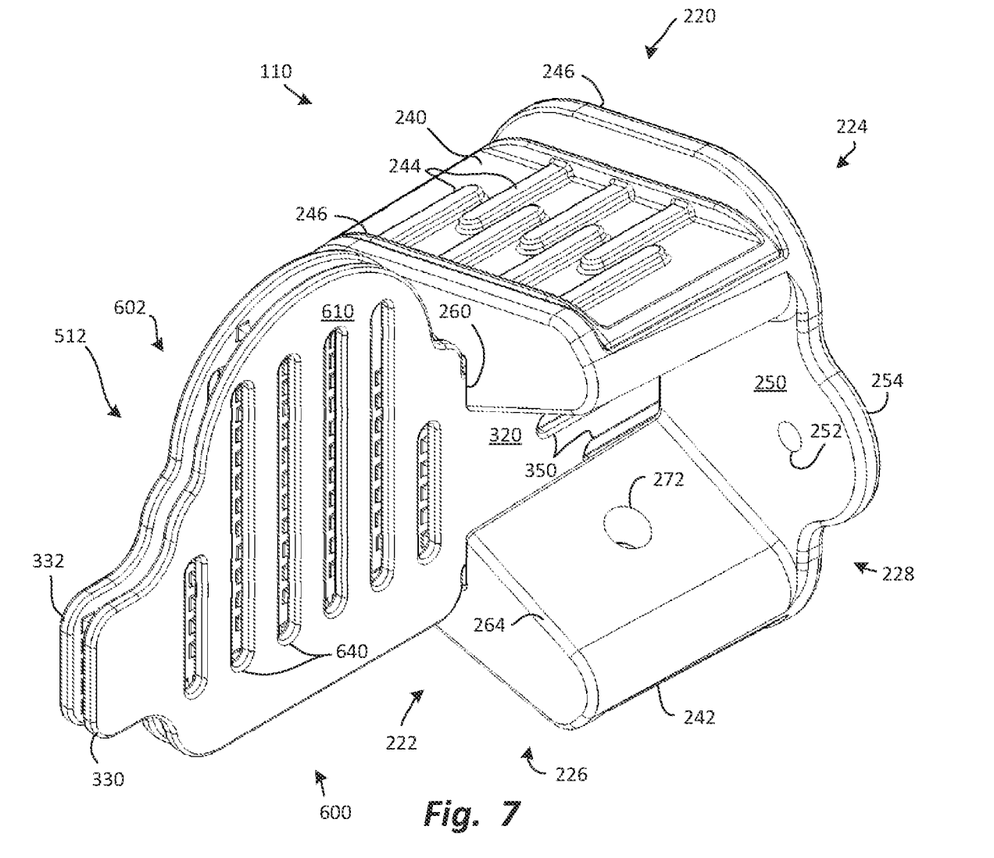
FIG. 7 is a perspective view of the mouth prop and frame of the aspiration prevention system of FIG. 5.

FIG. 7 is a perspective view of the mouth prop 110 and frame 512 of the aspiration prevention system 500 of FIG. 5. As in FIG. 4, the frame 112 is in the closed position, attached to the mouth prop 110, but the barrier 114 has been omitted.

The mouth prop 110 may oriented generally along the anterior-posterior direction, with some angulation due to the fact that the mouth 102 is wider posteriorly than it is anteriorly. In the aspiration prevention system 100 and the aspiration prevention system 500, this may cause the frame 112, the frame 512, and the barrier 114 to be angled such that the first flange 330 and the second flange 332 are posterior to the first tab 320 and the second tab 322. In some embodiments, it may be desirable to angle a frame and/or barrier nonparallel to a mouth prop so that their left and right sides are aligned with each other in the anterior-posterior direction. This may provide greater comfort for the user and/or enhanced aspiration protection.

In alternative embodiments, it may be desirable to increase the anterior/posterior differential between the ends of the frame 512 within the mouth 102. For example, when the practitioner is working on molars or adjacent gums on the opposite side of the mouth 102 from the mouth prop 110, it may be desirable to position the first flange 330 and the second flange 332 further posteriorly, to provide greater maneuvering room in that region of the mouth 102.

Such angulation may be accomplished in a variety of ways. According to one embodiment (not shown), the mouth prop 110 may be modified such that the slot 260 does not extend perpendicular to the buccal side 224 and the lingual side 226, but is rather angled such that the slot 260 intersects the buccal side 224 closer to the anterior end 228 than the location at which the slot 260 intersects the lingual side 226. The frame 112 or the frame 512 may then extend at an offset from perpendicularity with the mouth prop 110 that positions the first flange 330 and the second flange 332 at a posterior offset relative to the first tab 320 and the second tab 322 to provide more operating room in that region of the mouth 102.

In alternative embodiments, the frame 112 and/or the frame 512 may be modified to provide angulation to accomplish this without changing the orientation of the slot 260 of the mouth prop 110. One such embodiment will be shown and described in connection with FIGS. 8, 9A, and 9B.

Figure 8:
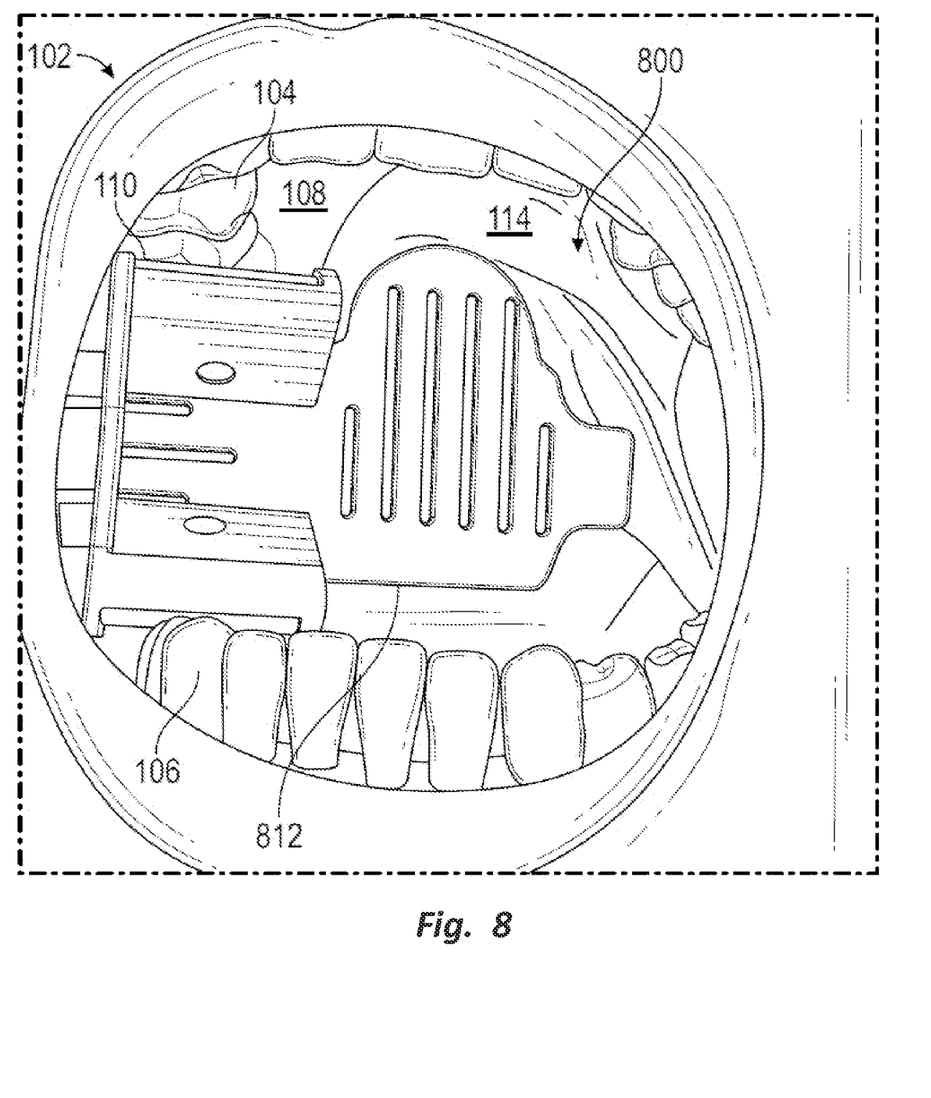
FIG. 8 is a perspective view of an aspiration prevention system according to another embodiment, in a mouth of a patient.

FIG. 8 is a perspective view of an aspiration prevention system 800 according to another embodiment, in a mouth 102 of a patient. Like the aspiration prevention system 100 of FIGS. 1 through 4, and the aspiration prevention system 500 of FIGS. 5 through 7, the aspiration prevention system 800 may include a mouth prop 110, a frame 812, and a barrier 114. The mouth prop 110 and the barrier 114 may be the same as in the aspiration prevention system 100 and the aspiration prevention system 500, although the barrier 114 may again optionally be omitted. The frame 812 may be shaped differently from the frame 112 and the frame 512, as will be shown in greater detail in FIGS. 9A and 9B.

Figure 9A:
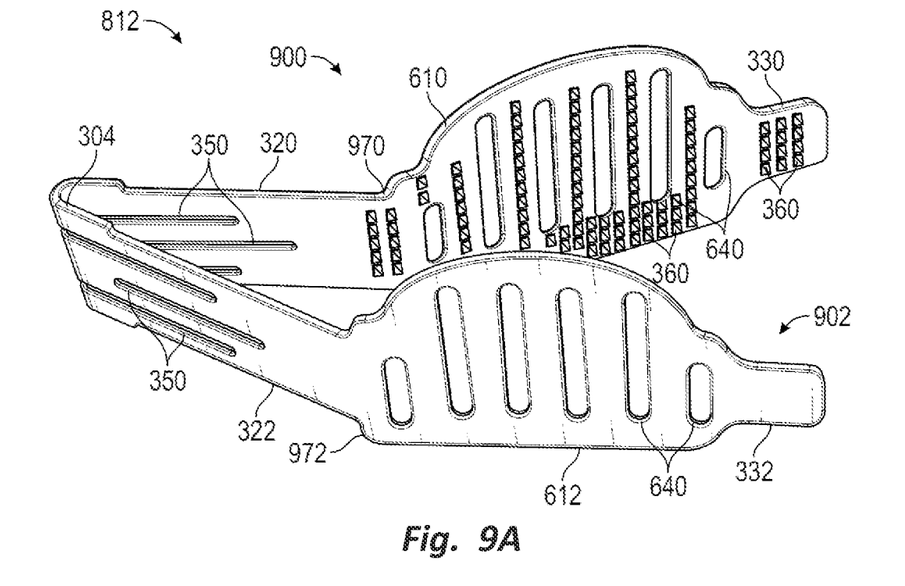
FIG. 9A is a perspective view of the frame of the aspiration prevention system of FIG. 8, in a partially folded position.

FIG. 9A is a perspective view of the frame 812 of the aspiration prevention system 800 of FIG. 8, in a partially folded position. As shown, the frame 812 may have a first arm 900 and a second arm 902. The first arm 900 and the second arm 902 may be connected together via a hinge 304, like the first arm 600 and the second arm 602 of the frame 512. The first arm 900 and the second arm 902 may also have a first grip portion 610 and a second grip portion 612 that are shaped like their counterparts of the frame 512.

However, the first arm 900 and the second arm 902 may have a first bend 970 and a second bend 972, respectively. The first bend 970 may cause the first grip portion 610 to be non-coplanar with the first tab 320, and the second bend 972 may similarly cause the second grip portion 612 to be non-coplanar with the second tab 322. The first bend 970 and the second bend 972 may optionally provide the same angle such that the first grip portion 610 and the second grip portion 612 are parallel to each other in the folded position, although they are not parallel to the first tab 320 and the second tab 322. This angle may be, for example, within the range of 5° to 45°. More precisely, this angle may be within the range of 10° to 35°. Yet more precisely, this angle may be within the range of 15° to 30°. Still more precisely, this angle may be within the range of 20° to 25°. This angle may, for example, be about 22.5°.

Figure 9B:
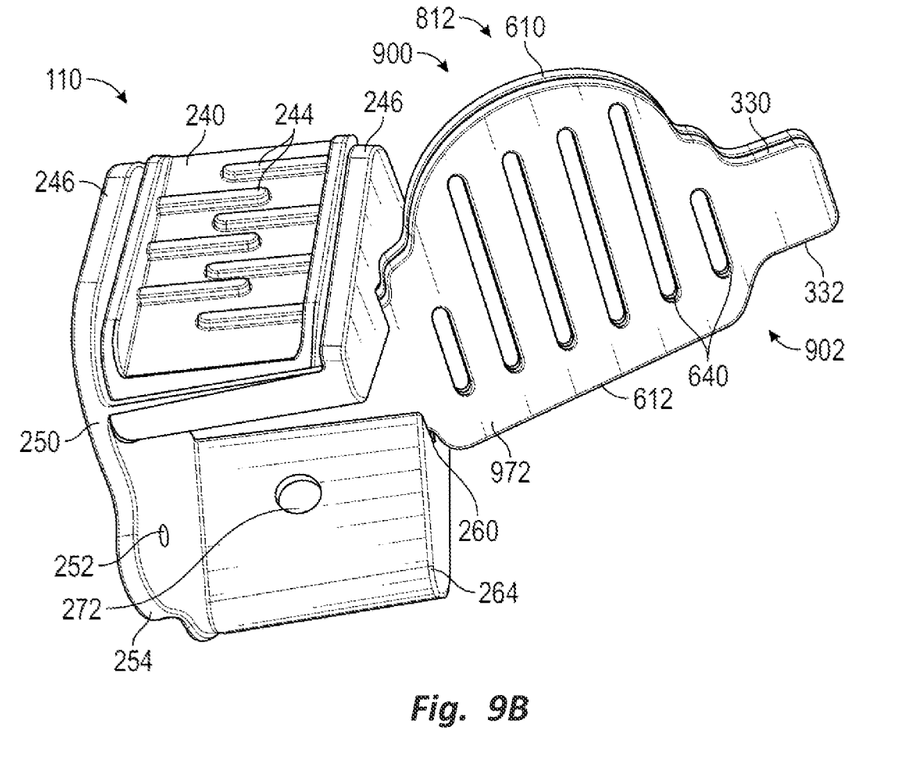
FIG. 9B is a perspective view of the mouth prop and frame of the aspiration prevention system of FIG. 8.

FIG. 9B is a perspective view of the mouth prop 110 and frame 812 of the aspiration prevention system 800 of FIG. 8. As shown, the first bend 970 and the second bend 972 may cause the first grip portion 610 and the second grip portion 612 to extend toward the posterior end 230 of the mouth prop 110 to provide greater maneuvering room in the posterior region of the mouth 102, on the side opposite to the mouth prop 110.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. An aspiration prevention system configured to keep items from moving from a mouth of a patient into a throat of the patient, the aspiration prevention system comprising:
a mouth prop comprising:
　a top surface configured to abut top teeth of the mouth;
　a bottom surface configured to abut bottom teeth of the mouth; and
　a frame coupling feature; and
a frame comprising:
　a barrier retention feature configured to retain an air-permeable barrier; and
　a prop coupling feature that is attachable to the frame coupling feature of the mouth prop in a position in which the frame at least partially covers the throat;
wherein the barrier retention feature comprises one or more holes that permit airflow between the throat and the mouth, through the one or more holes and through the air-permeable barrier.

2. The aspiration prevention system of claim 1, wherein the frame comprises:
a first arm;
a second arm; and
a hinge configured to permit the second arm to pivot relative to the first arm such that the frame comprises:
　an unfolded configuration in which the first arm is displaced from the second arm to permit insertion of the air-permeable barrier between the first arm and the second arm; and
　a folded configuration in which the first arm and the second arm extend adjacent to each other to capture the air-permeable barrier between the first arm and the second arm,
wherein the prop coupling feature is attachable to the frame coupling feature in the folded configuration.

3. The aspiration prevention system of claim 2, wherein:
the frame coupling feature comprises a slot;
the prop coupling feature comprises:
　a first tab on the first arm, adjacent to the hinge; and
　a second tab of the second arm, adjacent to the hinge; and
the first tab, the second tab, and the hinge are insertable into the slot in the folded configuration.

4. The aspiration prevention system of claim 1, wherein:
the frame coupling feature comprises a slot; and the prop coupling feature comprises a tab of the frame that is slidable into the slot.

5. The aspiration prevention system of claim 1, wherein the mouth prop further comprises an airway aperture that permits airflow through the mouth prop with the frame coupling feature attached to the prop coupling feature.

6. The aspiration prevention system of claim 5, wherein:
the airway aperture provides airflow into a cavity of the mouth prop from the throat;
the frame coupling feature comprises a slot anterior to the cavity;
the prop coupling feature comprises a tab of the frame that is slidable into the slot; and
the tab comprises one or more holes that provide airflow between the cavity and the mouth.

7. The aspiration prevention system of claim 1, further comprising the air-permeable barrier, wherein the air-permeable barrier is formed of a fabric material.

8. An aspiration prevention system configured to keep items from moving from a mouth of a patient into a throat of the patient, the aspiration prevention system comprising:
a mouth prop comprising:
a top surface configured to abut top teeth of the mouth; and
a bottom surface configured to abut bottom teeth of the mouth;
an air-permeable barrier;
a frame configured to be attached to the mouth prop and configured to retain the air-permeable barrier, relative to the mouth prop, in a position in which the frame at least partially covers the throat;
a first arm;
a second arm; and
a hinge configured to permit the second arm to pivot relative to the first arm such that the frame comprises:
an unfolded configuration in which the first arm is displaced from the second arm to permit insertion of the air-permeable barrier between the first arm and the second arm; and
a folded configuration in which the first arm and the second arm extend adjacent to each other to capture the air-permeable barrier between the first arm and the second arm;
wherein the frame is configured to be attached to the mouth prop in the folded configuration.

9. The aspiration prevention system of claim 8, wherein:
the mouth prop comprises a slot;
the frame comprises:
a first tab on the first arm, adjacent to the hinge; and
a second tab of the second arm, adjacent to the hinge; and
the first tab, the second tab, and the hinge are insertable into the slot in the folded configuration.

10. The aspiration prevention system of claim 8, wherein the frame comprises one or more holes that permit airflow between the throat and the mouth, through the one or more holes and through the air-permeable barrier.

11. The aspiration prevention system of claim 8, wherein: the mouth prop further comprises:
a cavity;
a slot anterior to the cavity; and
an airway aperture adjacent to the cavity;
the airway aperture provides airflow into the cavity from the throat;
the frame comprises a tab that is slidable into the slot; and
the tab comprises one or more holes that provide airflow between the cavity and the mouth.

12. The aspiration prevention system of claim 8, wherein the air-permeable barrier is formed of a fabric material.

13. An aspiration prevention system configured to keep items from moving from a mouth of a patient into a throat of the patient, the aspiration prevention system comprising:
a mouth prop comprising:
a top surface configured to abut top teeth of the mouth;
a bottom surface configured to abut bottom teeth of the mouth; and
a frame coupling feature; and
a frame comprising:
one or more holes that permit airflow through the frame;
a prop coupling feature that is attachable to the frame coupling feature of the mouth prop in a position in which the frame at least partially covers the throat;
an air-permeable barrier, wherein the frame is configured to retain the air-permeable barrier;
a first arm;
a second arm; and
a hinge configured to permit the second arm to pivot relative to the first arm such that the frame comprises:
an unfolded configuration in which the first arm is displaced from the second arm to permit insertion of the air-permeable barrier between the first arm and the second arm; and
a folded configuration in which the first arm and the second arm extend adjacent to each other to capture the air-permeable barrier between the first arm and the second arm;
wherein the prop coupling feature is attachable to the frame coupling feature in the folded configuration.

14. The aspiration prevention system of claim 13, wherein:
the frame coupling feature comprises a slot;
the prop coupling feature comprises:
a first tab on the first arm, adjacent to the hinge; and
a second tab of the second arm, adjacent to the hinge; and
the first tab, the second tab, and the hinge are insertable into the slot in the folded configuration.

15. The aspiration prevention system of claim 13, wherein the mouth prop further comprises an airway aperture that permits airflow through the mouth prop with the frame coupling feature attached to the prop coupling feature.

16. The aspiration prevention system of claim 15, wherein:
the airway aperture provides airflow into a cavity of the mouth prop from the throat;
the frame coupling feature comprises a slot anterior to the cavity;
the prop coupling feature comprises a tab of the frame that is slidable into the slot; and
the tab comprises one or more holes that provide airflow between the cavity and the mouth.

* * * * *